(12) United States Patent
Kapur et al.

(10) Patent No.: US 9,381,062 B2
(45) Date of Patent: Jul. 5, 2016

(54) ELECTRO-MECHANICAL INTRAVASCULAR DEVICE

(75) Inventors: Terri Kapur, Sharon, MA (US); Sean Pruitt, Franklin, MA (US); Arnaz Malhi, Watertown, MA (US)

(73) Assignee: Covidien LP, Mansfield, MA (US)

( * ) Notice: Subject to any disclaimer, the term of this patent is extended or adjusted under 35 U.S.C. 154(b) by 1066 days.

(21) Appl. No.: 13/484,351

(22) Filed: May 31, 2012

(65) Prior Publication Data

US 2013/0325003 A1 Dec. 5, 2013

(51) Int. Cl.
*A61B 18/14* (2006.01)
*A61B 17/22* (2006.01)
*A61B 17/3207* (2006.01)
*A61B 17/32* (2006.01)
*A61B 18/00* (2006.01)

(52) U.S. Cl.
CPC ....... *A61B 18/1492* (2013.01); *A61B 17/22012* (2013.01); *A61B 17/320758* (2013.01); *A61B 17/320725* (2013.01); *A61B 2017/22061* (2013.01); *A61B 2017/22067* (2013.01); *A61B 2017/22094* (2013.01); *A61B 2017/320004* (2013.01); *A61B 2017/320733* (2013.01); *A61B 2018/0041* (2013.01); *A61B 2018/00202* (2013.01); *A61B 2018/1435* (2013.01); *A61B 2018/1467* (2013.01)

(58) Field of Classification Search
CPC ................ A61B 18/1492; A61B 2017/22061; A61B 2017/22067; A61B 2017/22094; A61B 2017/320004; A61B 2017/320733; A61B 2018/0041; A61B 2018/00202; A61B 2018/1435; A61B 2018/1467
See application file for complete search history.

(56) References Cited

U.S. PATENT DOCUMENTS

| | | | |
|---|---|---|---|
| 4,445,509 A | 5/1984 | Auth | |
| 4,686,982 A | 8/1987 | Nash | |
| 4,762,130 A | 8/1988 | Fogarty et al. | |
| 4,790,813 A | 12/1988 | Kensey | |
| 5,030,201 A | 7/1991 | Palestrant | |
| 5,074,841 A | 12/1991 | Ademovic et al. | |
| 5,135,531 A | 8/1992 | Shiber | |
| 5,306,244 A * | 4/1994 | Shiber ................... | A61B 8/12 600/585 |
| 5,366,436 A | 11/1994 | Gibney | |
| 5,376,074 A | 12/1994 | Buchbinder et al. | |
| 5,423,799 A | 6/1995 | Shiv | |
| 5,569,245 A * | 10/1996 | Guglielmi ........ | A61B 17/12022 606/32 |
| 5,649,941 A | 7/1997 | Lary | |
| 5,665,098 A | 9/1997 | Kelly et al. | |
| 5,843,103 A | 12/1998 | Wulfman | |
| 5,868,768 A | 2/1999 | Wicherski et al. | |
| 5,997,558 A | 12/1999 | Nash | |
| 6,066,153 A | 5/2000 | Lev | |
| 6,066,158 A | 5/2000 | Engelson et al. | |
| 6,156,046 A | 12/2000 | Passafaro et al. | |

(Continued)

*Primary Examiner* — Amanda Patton

(57) ABSTRACT

An occlusion treatment device is disclosed that is configured and dimensioned for the treatment of a lumen that is at least partially blocked by an occlusion. The occlusion treatment device comprises a catheter including a body portion with proximal and distal ends, at least one expandable element that is secured to the body portion of the catheter, and a material removal element that extends distally from the distal end of the body portion including a debriding member in communication with an energy source to facilitate selective energizing of the debriding member. The catheter is axially movable through the lumen, and rotatable within the lumen, such that the material removal element selectively imparts non-mechanical and/or mechanical energy to the occlusion to effect debriding of the occlusion.

20 Claims, 8 Drawing Sheets

(56) References Cited

U.S. PATENT DOCUMENTS

| | | |
|---|---|---|
| 6,206,852 B1 | 3/2001 | Lee |
| 6,224,570 B1 | 5/2001 | Le et al. |
| 6,251,121 B1 | 6/2001 | Saadat |
| 6,451,036 B1 | 9/2002 | Heitzmann et al. |
| 6,491,660 B2 | 12/2002 | Guo et al. |
| 6,500,186 B2 | 12/2002 | Lafontaine et al. |
| 6,533,753 B1 | 3/2003 | Haarstad et al. |
| 6,554,827 B2 | 4/2003 | Chandrasekaran et al. |
| 6,572,630 B1 | 6/2003 | McGuckin, Jr. et al. |
| 6,579,299 B2 | 6/2003 | McGuckin, Jr. et al. |
| 6,702,782 B2 | 3/2004 | Miller et al. |
| 6,740,096 B2 * | 5/2004 | Teague ............... A61B 17/221 606/127 |
| 6,758,851 B2 | 7/2004 | Shibor |
| 6,808,531 B2 | 10/2004 | Lafontaine et al. |
| 6,818,002 B2 | 11/2004 | Shiber |
| 6,824,545 B2 | 11/2004 | Sepetka et al. |
| 6,824,550 B1 | 11/2004 | Noriega et al. |
| 6,843,797 B2 | 1/2005 | Nash et al. |
| 6,852,097 B1 | 2/2005 | Fulton, III |
| 6,926,725 B2 | 8/2005 | Cooke et al. |
| 7,008,381 B2 | 3/2006 | Janssens |
| 7,291,154 B2 | 11/2007 | Maitland et al. |
| 7,367,982 B2 | 5/2008 | Nash et al. |
| 7,416,555 B2 | 8/2008 | Krivoruchko |
| 7,479,147 B2 | 1/2009 | Honeycutt et al. |
| 7,507,246 B2 | 3/2009 | McGuckin et al. |
| 7,534,249 B2 | 5/2009 | Nash et al. |
| 7,628,763 B2 | 12/2009 | Noriega et al. |
| 7,744,604 B2 | 6/2010 | Maitland et al. |
| 7,766,049 B2 | 8/2010 | Miller et al. |
| 7,771,445 B2 | 8/2010 | Heitzmann et al. |
| 7,842,055 B2 | 11/2010 | Pintor et al. |
| 7,981,129 B2 | 7/2011 | Nash et al. |
| 8,016,799 B2 | 9/2011 | Nash et al. |
| 8,025,655 B2 | 9/2011 | Kugler et al. |
| 8,034,023 B2 | 10/2011 | Wahr et al. |
| 8,043,312 B2 | 10/2011 | Noriega et al. |
| 8,043,314 B2 | 10/2011 | Noriega et al. |
| 8,062,258 B2 | 11/2011 | Demarais et al. |
| 2005/0119615 A1 | 6/2005 | Noriega |
| 2008/0097499 A1 | 4/2008 | Nash |
| 2009/0138031 A1 | 5/2009 | Tsukernik |
| 2011/0046542 A1 | 2/2011 | Evans et al. |
| 2011/0208222 A1 | 8/2011 | Ljahnicky |

\* cited by examiner

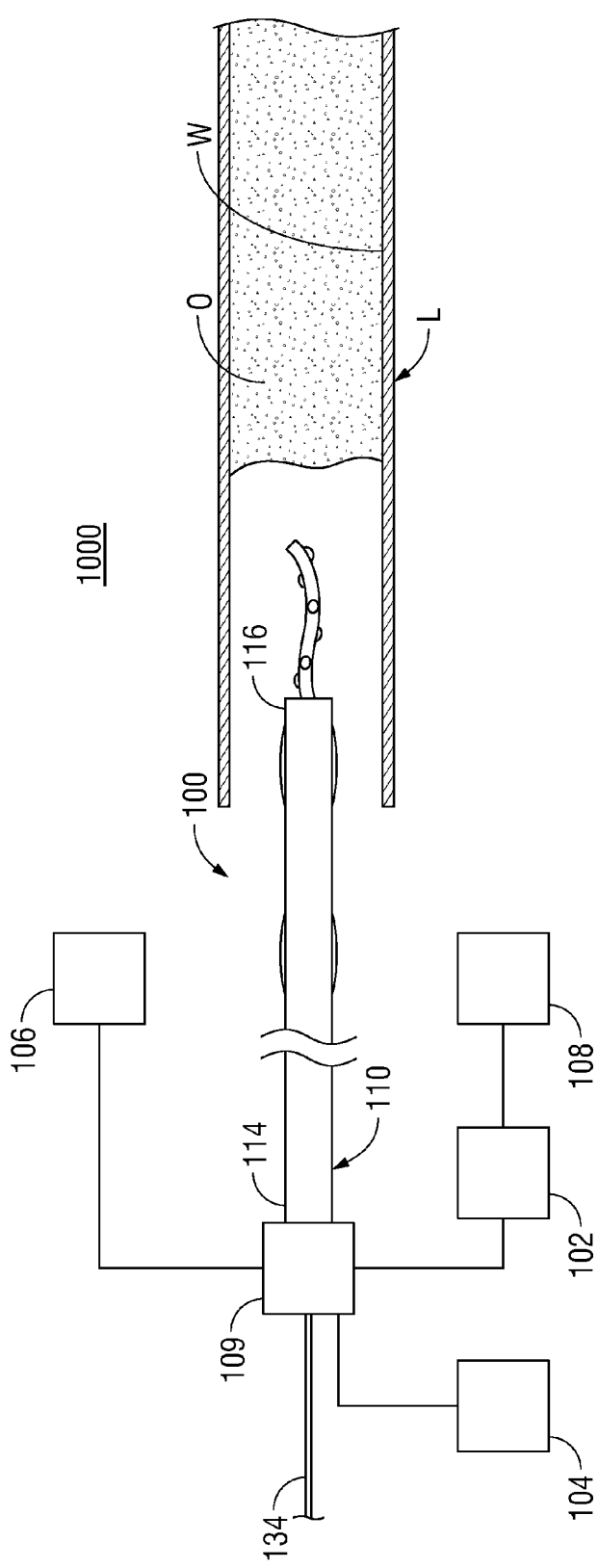
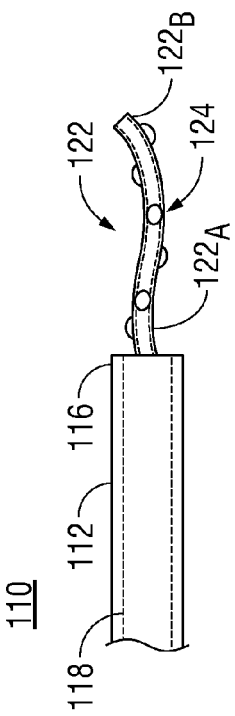

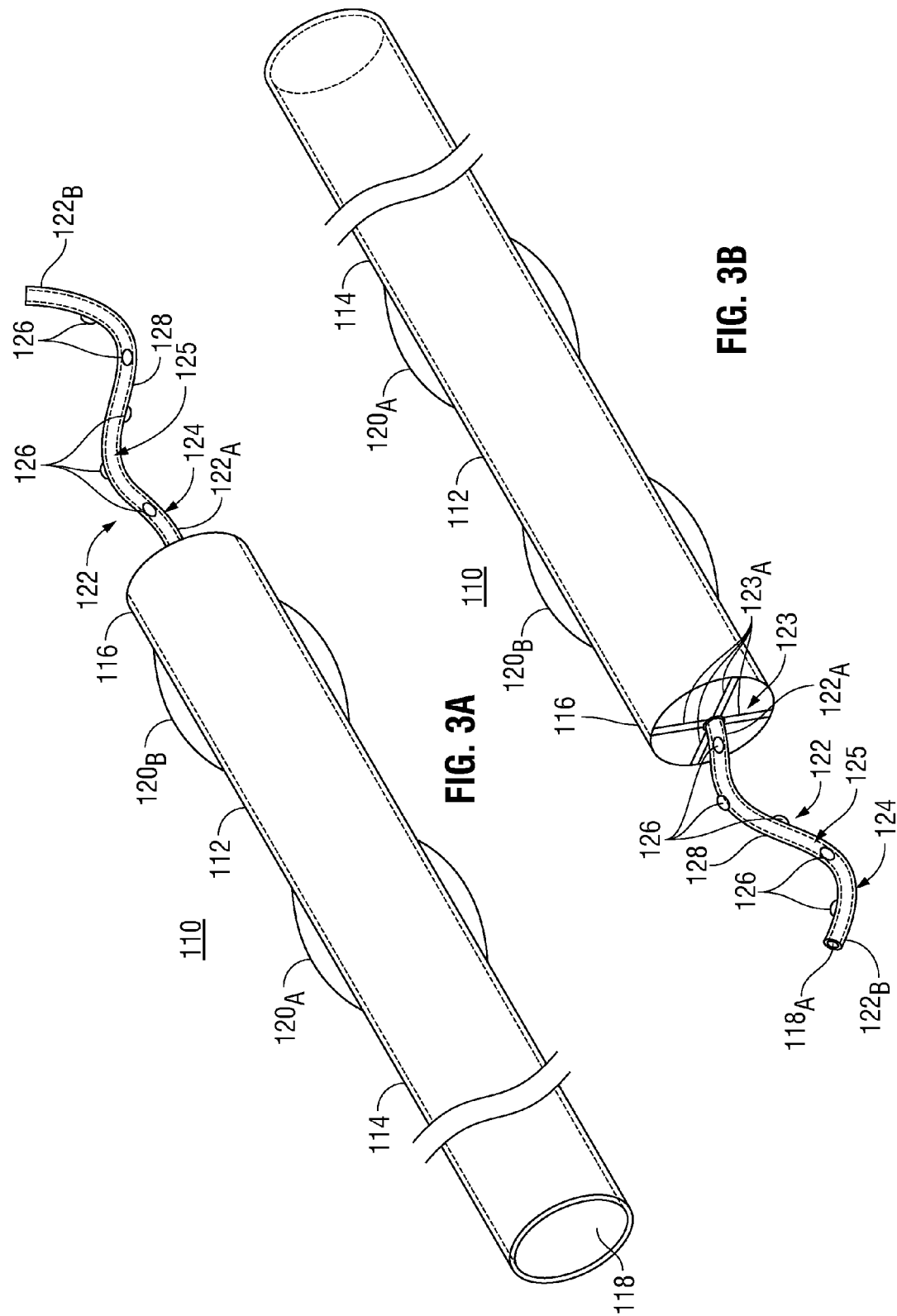

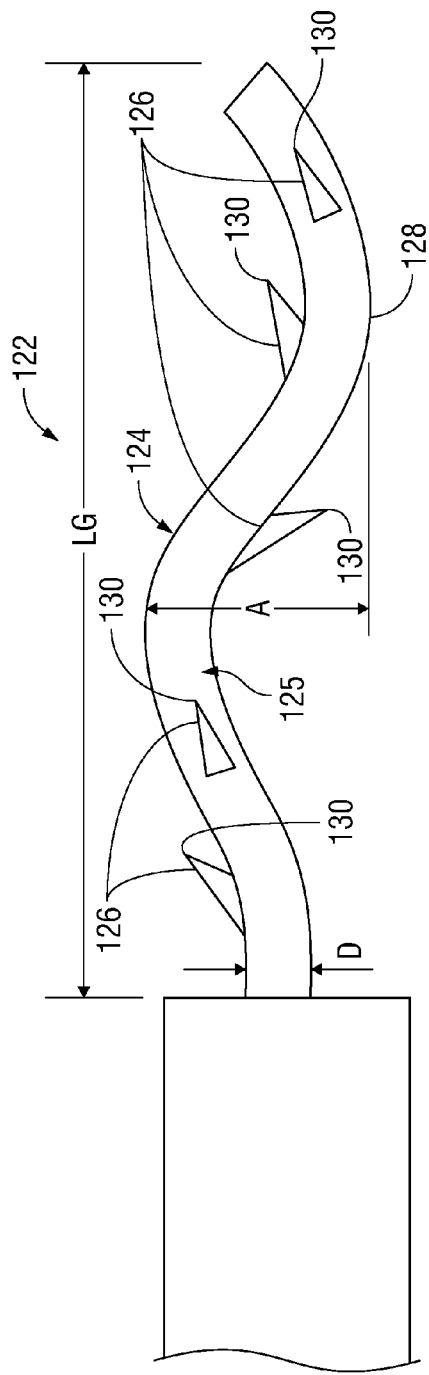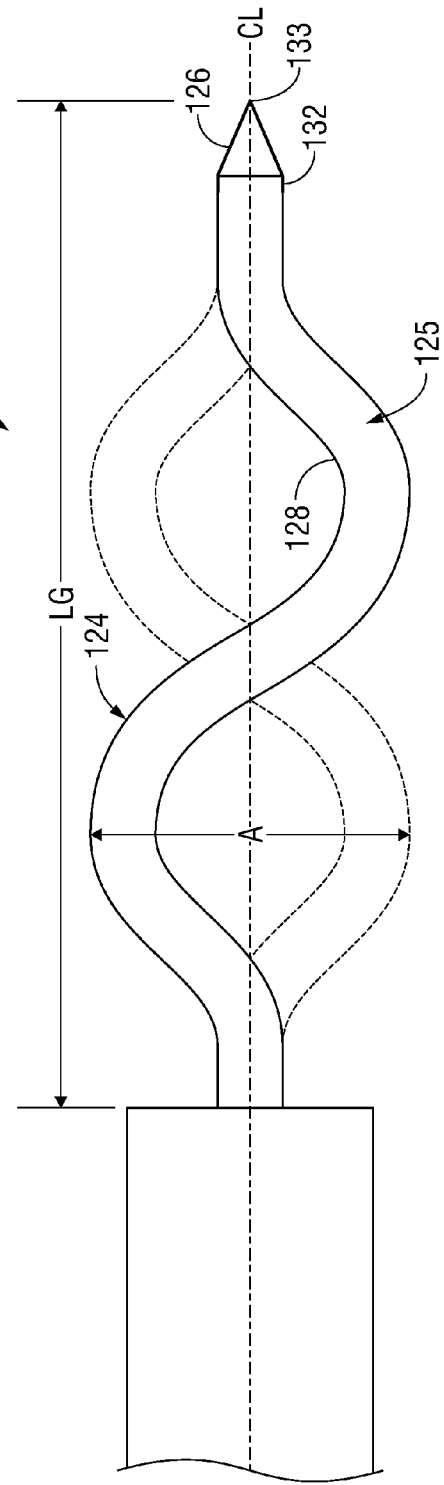
FIG. 5A
FIG. 5B

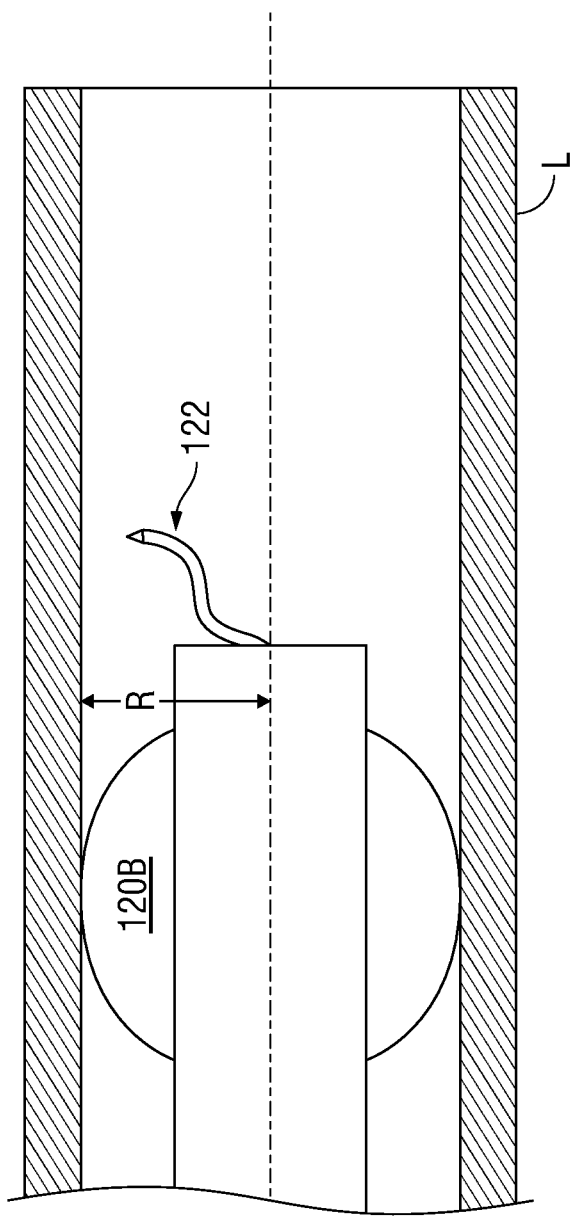

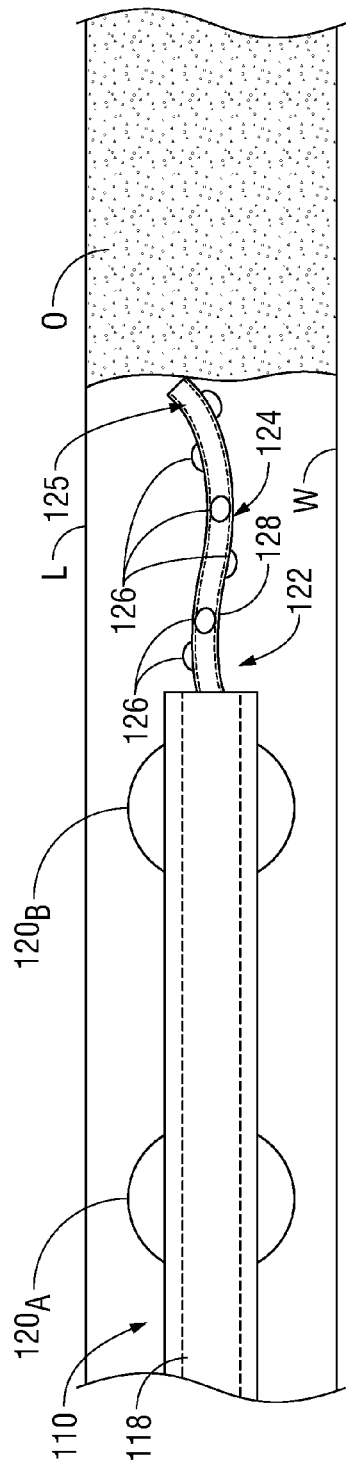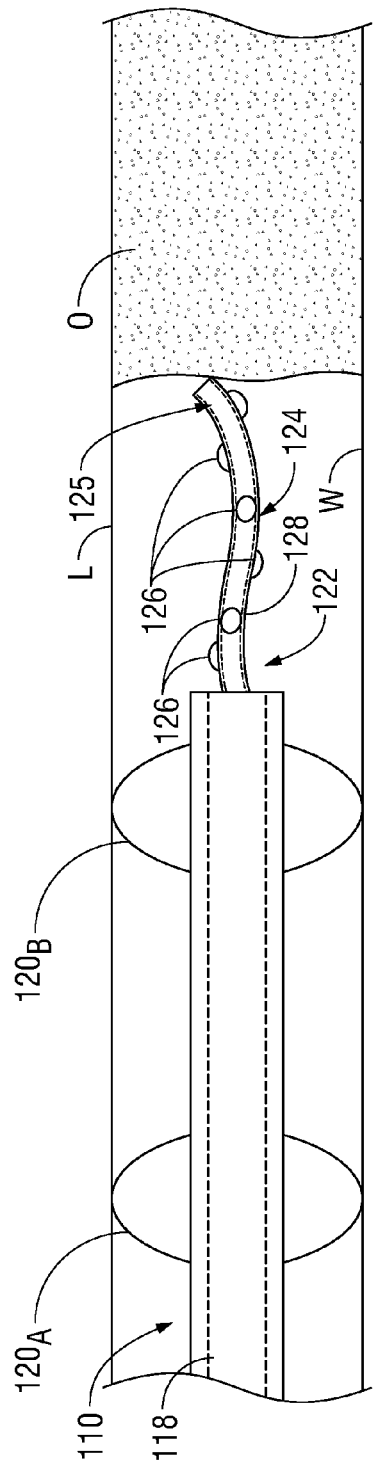

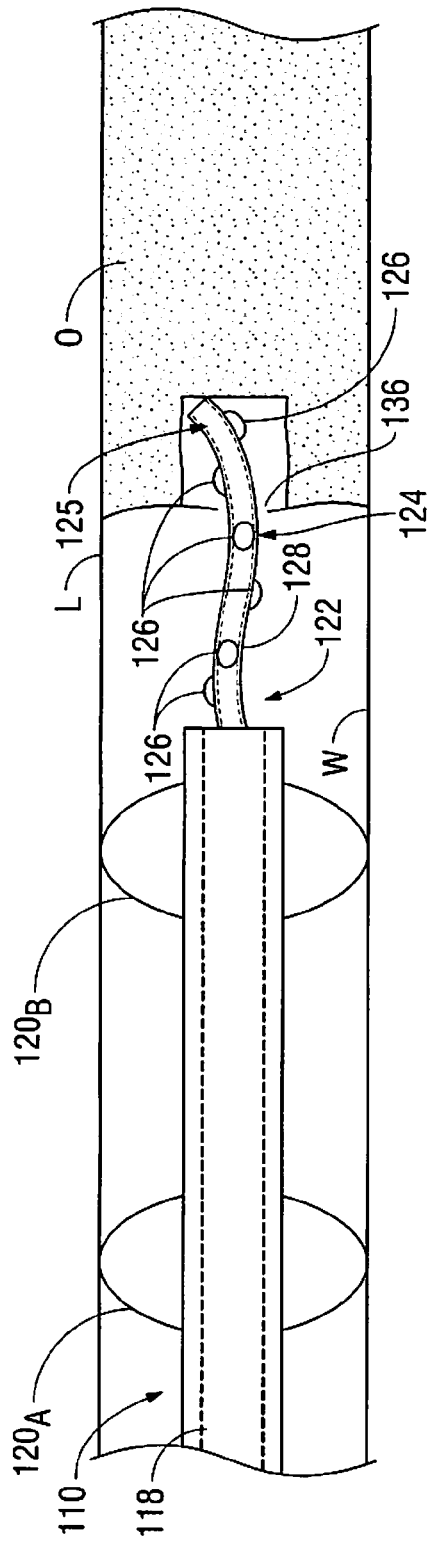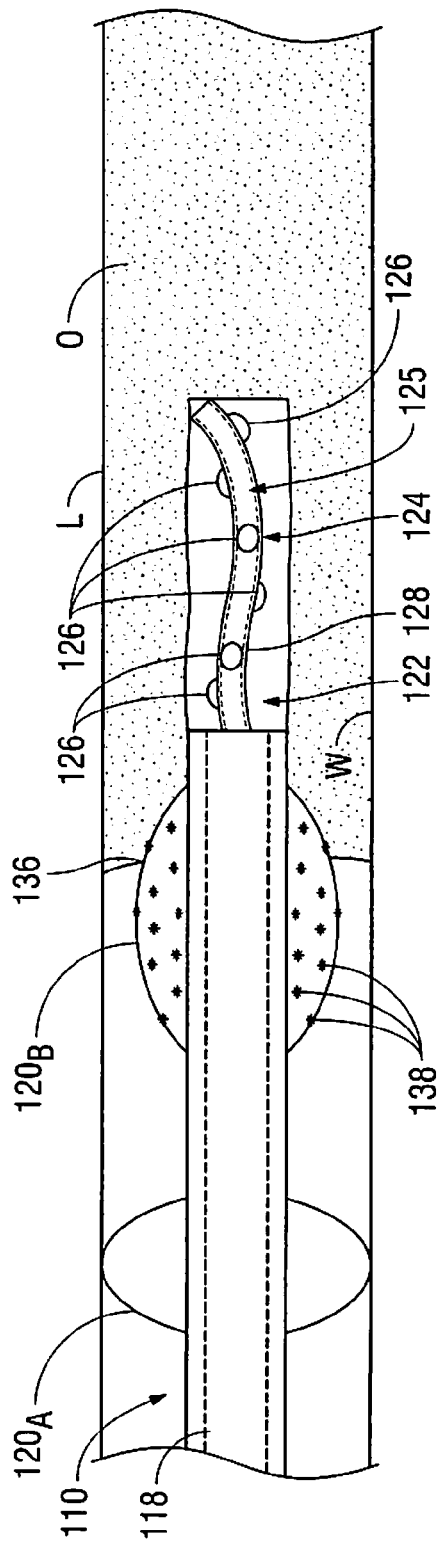

ELECTRO-MECHANICAL INTRAVASCULAR DEVICE

BACKGROUND

1. Technical Field

The present disclosure relates to systems, apparatus, and methods for the treatment of occlusions within a lumen, such as a blood vessel, and more specifically to an electro-mechanical intravascular device. In one specific aspect of the disclosure, an intravascular occlusion treatment device is described, as well as corresponding methods of use.

2. Background of Related Art

Apparatus and methods used to establish, and/or maintain, patency in a lumen are well known in the art. For example, electrosurgical apparatus, which are generally classified as either monopolar or bipolar, treat occlusions via the application of energy, such as, for example, electrical (RE) energy, microwave energy, or resistive heating.

Monopolar electrosurgical apparatus typically include an active electrode forming part of a handheld device, and a return electrode located remotely from the handheld device that is in contact with the patient in order to transmit energy back to the source supplying the apparatus. For example the return electrode may be configured as a pad positioned beneath the patient.

By contrast, in bipolar electrosurgical apparatus, the handheld device typically includes both an active electrode and a return electrode. During the use of such devices, the active electrode and the return electrode are placed in close proximity so as to establish an electrical circuit between the two electrodes. The target tissue is positioned between the active electrode and the return electrode so as to limit the application of electrical current to the target tissue, and minimize the effect, if any, on collateral tissue(s) adjacent the target tissue.

The handheld devices of monopolar electrosurgical apparatus are usually of simpler construction when compared to those of bipolar electrosurgical apparatus, since the handheld devices of monopolar electrosurgical apparatus include only an active electrode. However, with monopolar electrosurgical apparatus devices, it is generally more difficult to limit the area to which energy is applied, and thus, to confine the application of energy to the target tissue.

Also understood in the art is the fact that certain methods of removal are more suited for specific types of occlusions. For example, a single clot may include various tissue types that require different methods of treatment, and in the context of chronic clots, the sole use of a chemical agent, such as a tissue plasminogen activator (tPA), may not achieve the desired result. Since the morphology of occlusive tissue is typically unknown prior to the initiation of a removal procedure, an occlusion treatment device facilitating various methods of treatment remains desirable.

SUMMARY

In one aspect of the present disclosure, an occlusion treatment device is disclosed that is configured and dimensioned for the treatment of a lumen that is at least partially blocked by an occlusion. The treatment device comprises a catheter including a body portion with proximal and distal ends, at least one expandable element that is secured to the body portion of the catheter, and a flexible material removal element extending distally from the distal end of the body portion that includes a debriding member having a free distal end configured and dimensioned to contact the occlusion, and being in communication with an energy source to facilitate selective energizing of the debriding member, for example, through the inclusion of one or more electrodes in communication with the energy source. The catheter is dimensioned to be axially movable through the lumen, and rotatable within the lumen, such that the material removal element selectively imparts non-mechanical and/or mechanical energy to effect debriding of the occlusion.

In one embodiment of the disclosure, it is envisioned that the body portion of the catheter and the material removal element may be formed from different materials. For example, the material comprising the material removal element may be more rigid than the material comprising the body portion of the catheter.

It is also envisioned that the occlusion treatment device may include both a proximal expandable element, and a distal expandable element. In such embodiments, the proximal and distal expandable elements may be in fluid communication with a common source of fluid. Alternatively, however, the proximal and distal expandable elements may be configured and dimensioned for independent expansion such that the distal expandable element is expandable to a lesser extent than the proximal expandable element, whereby the distal expandable element is configured and dimensioned for insertion into the opening in the occlusion created during debriding of the occlusion.

It is further envisioned that the proximal and distal expandable elements may be formed from different materials. For example, the material comprising the distal expandable element may be more rigid than the material comprising the proximal expandable element.

Additionally, or alternatively, it is envisioned that the distal expandable element may include at least one cutting element to facilitate debriding of the occlusion, and creation of an opening in the occlusion.

In another aspect of the present disclosure, an occlusion treatment system is disclosed comprising an energy source, an occlusion treatment device that includes a catheter with a body portion having a passageway extending longitudinally therethrough, and a material removal element movable through the body portion of the catheter that includes a flexible debriding member having a free distal end configured and dimensioned to contact the occlusion, and being in communication with the energy source to facilitate selective energizing of the debriding member, for example, through the inclusion of one or more electrodes in communication with the energy source. The material removal element is configured and dimensioned for axial movement through the passageway of the catheter, as well as rotational movement relative to the catheter, such that the material removal element is selectively positionable to impart non-mechanical and/or mechanical energy to the occlusion to effect debriding of the occlusion.

It is envisioned that that occlusion treatment system may further include a ground element in communication with the energy source that is configured and dimensioned for contact with a patient's tissue.

It is further envisioned that the occlusion treatment device may include at least one expandable element, for example, a proximal expandable element, and a distal expandable element. In such embodiments, the proximal and distal expandable elements may be configured and dimensioned for independent expansion such that the distal expandable element is expandable to a lesser extent than the proximal expandable element, whereby the distal expandable element is configured and dimensioned for insertion into an opening in the occlusion created during debriding of the occlusion.

It is also envisioned that the proximal and distal expandable elements may be formed from different materials. For example, the material comprising the distal expandable element may be more rigid than the material comprising the proximal expandable element.

Additionally, or alternatively, the distal expandable element may include at least one cutting element to facilitate debriding of the occlusion, and enlargement of the opening.

In yet another aspect of the disclosure, a method is disclosed for treating a lumen that is at least partially blocked by an occlusion. The method includes positioning an occlusion treatment device within the lumen, advancing the occlusion treatment device through the lumen until a free distal end of a flexible material removal element of the device is positioned adjacent the occlusion, expanding an expandable element of the occlusion treatment device, penetrating the occlusion with the free distal end of the material removal element to create an opening, delivering non-mechanical energy to the material removal element, advancing the material removal element distally through the opening, and manipulating the material removal element to impart non-mechanical and/or mechanical energy to the occlusion to effect debriding of the occlusion, and enlargement of the opening.

It is envisioned that manipulating the material removal element may include rotating the material removal element, and/or effecting axial movement of the material removal element.

It is further envisioned that expanding the expandable element may include expanding a proximal expandable element to center the occlusion treatment device within the lumen, and expanding a distal expandable element. Such embodiments of use may include expanding the proximal expandable element to a first extent, and expanding the distal expandable element to a second, lesser extent.

The disclosed method may further include advancing the occlusion treatment device through the lumen such that the expandable element is at least partially positioned within the opening, as well as mechanically debriding the occlusion using the expandable element. For example, mechanically debriding the occlusion may include engaging the occlusion with one or more cutting elements included on the expandable element.

In still another aspect of the present disclosure, an occlusion treatment device is disclosed that is configured and dimensioned for treatment of a lumen at least partially blocked by an occlusion. The occlusion treatment device includes a catheter having a body portion with proximal and distal ends, at least one expandable element secured to the body portion of the catheter that is capable of being expanded within the lumen to define a radial dimension, and a material removal element that extends distally from the distal end of the body portion.

The material removal element includes a flexible debriding member defining a length that is less than the radial dimension in order to restrict contact between the debriding member and an inner wall of the lumen.

It is envisioned that the debriding member may include a free distal end that is configured and dimensioned to contact the occlusion.

The material removal element may also be in communication with an energy source to facilitate selective energizing of the debriding member.

Additionally, it is envisioned that the catheter may be dimensioned to be axially movable through the lumen, and/or rotatable within the lumen, such that the material removal element selectively imparts non-mechanical and/or mechanical energy to the occlusion to effect debriding of the occlusion.

In another aspect of the present disclosure, an occlusion treatment device is disclosed that is configured and dimensioned for treatment of a lumen at least partially blocked by an occlusion. The occlusion treatment device includes a catheter with a body portion having proximal and distal ends, and a material removal element that extends distally from the distal end of the body portion. The material removal portion includes a flexible debriding member having a non-linear configuration defining an amplitude that varies along a length of the debriding member, and a free distal end that is configured and dimensioned to contact the occlusion.

It is envisioned that the amplitude defined by the debriding member may decrease in a distal direction, and/or that the the material removal element may be in communication with an energy source to facilitate selective energizing of the debriding member.

It is also envisioned that the catheter may be dimensioned to be axially movable through the lumen, and/or rotatable within the lumen, such that the material removal element selectively imparts non-mechanical and/or mechanical energy to the occlusion to effect debriding of the occlusion.

It is further envisioned that the occlusion treatment device may include at least one expandable element secured to the body portion of the catheter that is expandable within the lumen in order to center the catheter therein, and maintain the catheter in a desired position.

BRIEF DESCRIPTION OF THE DRAWINGS

Various embodiments of the present disclosure are described herein with reference to the drawings wherein:

FIG. 1 is a schematic view illustrating an occlusion treatment system including an occlusion treatment device according to one embodiment of the present disclosure;

FIG. 2 is a partial, side view of the occlusion treatment device seen in FIG. 1;

FIGS. 3A and 3B are partial side, perspective views of the occlusion treatment device;

FIG. 5A is a partial, side view illustrating a material removal element of the occlusion treatment device according to one embodiment of the disclosure;

FIG. 5B is a partial, side view illustrating a material removal element of the occlusion treatment device according to another embodiment of the disclosure;

FIG. 5C is a partial, schematic side view of an alternative embodiment of the occlusion treatment device positioned within the lumen;

FIG. 6 is a partial, schematic side view of the occlusion treatment device positioned within a lumen, and in contact with an occlusion, prior to expansion of proximal and distal expandable elements;

FIG. 7 is a partial, schematic side view of the occlusion treatment device positioned within the lumen, and in contact with the occlusion, following expansion of the proximal and distal expandable elements;

FIG. 8 is a partial, schematic side view of the occlusion treatment device with the material removal element partially advanced through an opening created in the occlusion; and FIG. 9 is a partial, schematic side view illustrating an alternative embodiment of the occlusion treatment device shown advanced through an opening created in the occlusion such that the distal expandable element contacts the occlusion.

DESCRIPTION OF THE EMBODIMENTS

Figure 4:
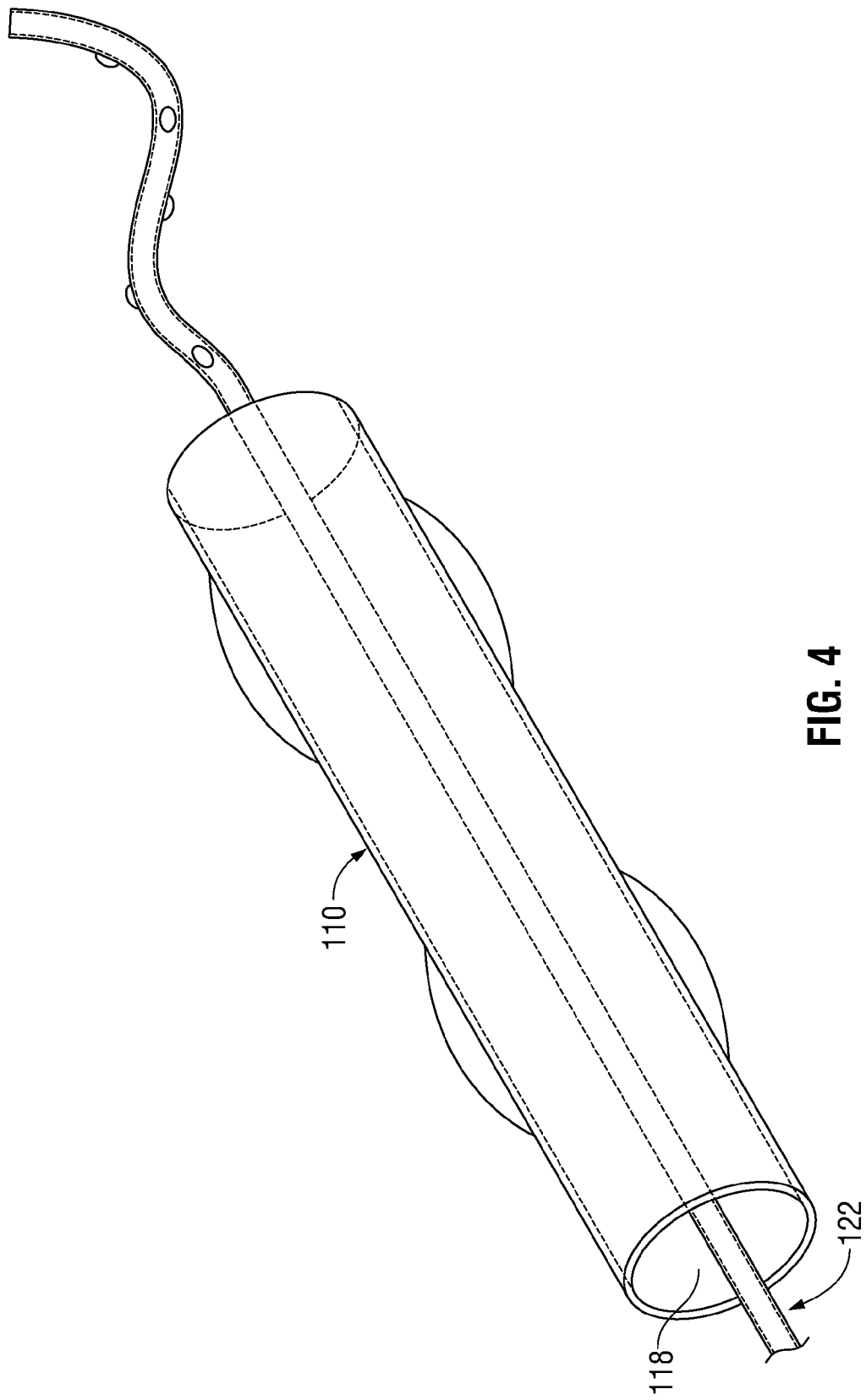
FIG. 4 is a partial side, perspective view of an alternative embodiment of the occlusion treatment device.

Embodiments of the presently disclosed material removal system will now be described in detail with reference to the drawings wherein like reference numerals identify similar or identical elements. As used herein, the term "distal" refers to that portion of the presently disclosed occlusion treatment system, or component thereof, that is furthest from the user, such as a physician, during proper use, while the term "proximal" refers to that portion of the occlusion treatment system, or component thereof, that is closest to the user during proper use. Additionally, the term "lumen" should be understood to include any lumen within the body, either natural or artificial, such as, for example, blood vessels, blood vessel grafts, fistulas, and the like. Moreover, the term "occlusion" should be understood to encompass any partial or total blockage of a lumen, such as, for example, thrombus, atheromas, plaque, and the like. Finally, as used herein below, the terms "debride" and "debriding" in the context of treating an occlusion should be understood to include various mechanical and non-mechanical methods of treating the occlusion, including, but not limited to abrading, softening, melting, or otherwise breaking up the occlusion.

Throughout the following description, well known functions and constructions are not described in detail so as to avoid obscuring the present disclosure in unnecessary detail.

FIG. 1 is a schematic illustration of an occlusion treatment system 1000 according to one embodiment of the present disclosure useful in the treatment of lumen L that is at least partially blocked by an occlusion O. The occlusion treatment system 1000 includes a monopolar occlusion treatment device 100, an energy source 102, a ground element 104, a source of pressurized fluid 106, for example, saline, a fluid suction/supply device 108, and a control unit 109.

With reference to FIGS. 2-3B as well, the occlusion treatment device 100 includes a catheter 110 having a body portion 112 with respective proximal and distal ends 114, 116, and a passageway 118 that extends longitudinally through the catheter 110. The catheter 110 further includes a pair of expandable elements $120_A$, $120_B$ that are secured to the body portion 112, and a material removal element 122 with a debriding member 124.

The body portion 112 of the catheter 110 may be formed from any suitable biocompatible material sufficiently pliable to facilitate insertion of the catheter 110 into the lumen L. Suitable materials include, but are not limited to, polymeric materials, elastomeric materials, for example, silicone and fabric materials, or a synthetic resin, for example, polyurethane, polyethylene, polypropylene, nylons, polytetrafluoroethylene (PTFE), polyether ether ketone (PEEK), or polyimide. It is envisioned that the body portion 112 of the catheter 110 may include one or more ports (not shown) formed therein so as to facilitate the administration of a treatment agent, such as a thrombolytic agent, for example, tPA, to the occlusion O.

The passageway 118 extending through the catheter 110 is provided in fluid communication with the fluid suction/supply device 108 so as to facilitate infusion and aspiration, i.e., the supply of fluid to, and the withdrawal of fluid from, the target site, through the passageway 118. Specifically, during use of the disclosed occlusion treatment system 1000 in the course of a surgical procedure, the passageway 118 is utilized to remove fluid and debris from the target site, as described in further detail below. In an alternative embodiment, the catheter 110 may include two passageways, one in fluid communication with the supply side of the fluid suction/supply device 108, and one in fluid communication with the suction side of the fluid suction/supply device 108. In such an embodiment, one passageway may be larger to also accommodate passage of the material removal element 122. Further still, in another embodiment, the catheter 110 may include a third passageway through which the material removal element passes.

With continued reference now to FIGS. 1-3B, the expandable elements $120_A$, $120_B$ may be formed from any biocompatible material suitable for the intended purpose of permitting selective expansion of the expandable elements $120_A$, $120_B$. Examples of suitable materials include, but are not limited to, nylon, silicone, latex, polyolefin, vinyl, polyether block amide (e.g., PEBAX®) polyethylene, polyurethane, and polyethylene terephthalate (PET). It is envisioned that the expandable elements $120_A$, $120_B$ may be formed from the same material, or alternatively, that the expandable elements $120_A$, $120_B$ may be formed from different materials, as will be discussed in greater detail below.

The expandable elements $120_A$, $120_B$ are in communication with a source of fluid, such as, for example, the pressurized source of fluid 106 (FIG. 1), such that the expandable elements $120_A$, $120_B$ are movable between an initial position (FIG. 6), wherein the expandable elements $120_A$, $120_B$ define first transverse cross-sectional dimensions, and a subsequent position (FIG. 7), wherein the expandable elements $120_A$, $120_B$ define second, larger transverse cross-sectional dimensions. In the initial position, the smaller transverse cross-sectional dimensions of the expandable elements $120_A$, $120_B$, which may correspond to the outer transverse cross-sectional dimension of the body portion 112, facilitate insertion of the catheter 110 into the lumen L, and movement of the catheter 110 through the lumen L. In the subsequent position, the enlarged transverse cross-sectional dimensions of the expandable elements $120_A$, $120_B$ facilitate engagement with an internal wall W of the lumen L in order to center the catheter 110 within the lumen L, and maintain the catheter 110 in a desired position. By centering the catheter 110 within the lumen L, the internal wall W of the lumen L can be separated from the material removal element 122 of the catheter 110 in order to prevent inadvertent damage to the lumen L. For example, by expanding the expandable elements $120_A$, $120_B$, and centering the material removal element 122 of the catheter 110 within the lumen L, the material removal element 122 of the catheter 110 may be separated from the internal wall W of the lumen L, for example, by a distance of approximately 1.5 mm to approximately 2 mm. Although the catheter 110 is described herein below as including expandable elements $120_A$ and $120_B$, in alternative embodiments of the disclosure, it is envisioned that the catheter 110 may include either greater, or fewer, numbers of expandable elements dependent upon the nature of the procedure in which the occlusion treatment system 1000 is employed.

With reference now to FIGS. 1-4, the material removal element 122 may include a proximal end $122_A$ that is secured to the distal end 116 of the body portion 112 in cantilevered fashion, and a free, unsupported distal end $122_B$, as illustrated in FIGS. 1-3B, whereby relative axial movement between the material removal element 122 and the catheter 110 is inhibited. In such an embodiment, the passageway 118 would extend through the material removal element 122 through an opening 118A (see FIG. 3B). Preferably, however, the material removal element 122 may constitute a separate component of the occlusion treatment system 1000 that is inserted through the passageway 118 of the catheter 110 such that the material removal element 122 can be moved independently of the catheter 110, as seen in FIG. 4. For example, it is envisioned that the material removal element 122 may be displaced axially within the passageway 118 of the catheter 110, or another central passageway in a multi-passageway catheter, for movement between advanced and retracted positions, and/or rotated relative to the catheter 110.

As illustrated in FIG. 3B, it is envisioned that the proximal end $122_A$ of the material removal element 122 may be secured to the distal end 116 of the body portion 112 by a supporting structure 123, for example. Although illustrated as including a plurality of strut members $123_A$ that are secured to the body portion 112, it should be understood that, in alternate embodiments of the present disclosure, the supporting structure 123 may assume any configuration, and include any structural elements, suitable for the intended purpose of securing the proximal end $122_A$ of the material removal element 122 to the distal end 116 of the body portion 112.

The debriding member 124 of the material removal element 122 is configured, dimensioned, and adapted to debride, and/or penetrate, the occlusion O (FIG. 1), and may be formed from any biocompatible material suitable for this intended purpose. The debriding member 124 may be formed from the same material comprising the body portion 112 of the catheter 110, or alternatively, the debriding member 124 and the body portion 112 of the catheter may be formed from different materials. For example, the material comprising the debriding member 124 may have either greater, or lesser, flexibility than the material comprising the body portion 112 of the catheter 110, dependent upon the nature of the occlusion O, and the specific requirements of the procedure in which the occlusion treatment system 1000 is employed. In one specific embodiment, it is envisioned that the debriding member 124 may be formed from a flexible material facilitating oscillation, agitation, or deformation in a desired manner.

The debriding member 124 includes a body 125, and one or more electrodes 126 that are positioned on an outer surface 128 of the body 125. The electrode(s) 126 may be secured to the outer surface 128 of the body 125 of the debriding member 124 in any suitable manner. For example, it is envisioned that the electrode(s) 126 may be secured to the outer surface 128 of the body 125 of the debriding member 124 using an adhesive, or alternatively, that the electrode(s) 126 may be secured to the outer surface 128 of the debriding member 124 by overmolding, electrodeposition, crimping, or the like.

The electrode(s) 126 are in communication with the energy source 102 (FIG. 1), such as through an electrical conductor (not shown) extending along, or through, the body portion 112 or the material removal element 122. Communication between the electrode(s) 126 and the energy source 102 energizes the material removal element 122 by imparting the material removal element 122 with non-mechanical energy. It is envisioned that the energy source 102 may be capable of generating various types of non-mechanical energy suitable for the intended purpose of facilitating removal of the occlusion O (FIG. 1) including, but not being limited to, resistive heating, RF energy, microwave energy, ultrasonic energy, or the like.

Various configurations for the electrode(s) 126 are contemplated by the present disclosure in order to enhance the ability of the material removal element 122 to debride the occlusion O. For example, as seen in FIG. 5A, the electrode(s) 126 may have a substantially angular configuration with a distally positioned apex 130. Alternatively, as seen in FIG. 5B, it is envisioned that the electrode(s) 126 may have a conical configuration, and may be positioned adjacent a distal tip 132 of the material removal element 122. As seen in FIG. 5B, it is envisioned that the distal tip 132 may include an apex 133 that is substantially aligned with a centerline CL of the material removal element 122.

In the various embodiments illustrated in FIGS. 1-5B, the material removal element 122 is illustrated as a small diameter wire having a non-linear, wavy configuration, for example, a generally sinusoidal configuration, at the debriding member 124. In alternative embodiments of the disclosure, however, the debriding member 124 may assume alternative configurations, such as, for example, linear, helical, or the like. The wavy configuration at the debriding member 124 has the advantage of having a smaller cross section at any one point along the wire, but enables a larger opening to be made in the occlusion O by rotating the material removal element 122 (see, e.g., FIG. 5B). The smaller cross section of the wire making up the material removal element 122 at the debriding member 124 is better able to enter a total occlusion O and harder chronic occlusions. In general, the material removal element 122 and debriding member 124 may be less than 0.060 inches in diameter D, and more preferable around 0.035 inches.

The small diameter D and the flexibility of the material removal element 122 may enable the wavy debriding member 124 to at least partially deform and pass through the passageway 118 and resume its full wavy configuration once expelled out of the passageway 118 at the distal end 116 of the catheter 110. Referring to FIGS. 5B and 5C, the length LG of the maximum exposed distal portion of the material removal element 122 (e.g., the debriding member 124) may be less than the radius R of expandable element $120_B$ while inflated so that the debriding member 124 is less likely to bend, and less likely to interface with the lumen L if the debriding member 124 should bend. For example, the length LG of the debriding member may be 0.90 R, more preferably 0.75 R. Further, the outer diameter of the catheter 110 may be equal to or less than the maximum amplitude A of the wavy configuration of the debriding member 124 to enable the catheter 110 to follow the debriding member 125 through the opening made by the debriding member 124 in the occlusion O. As can be appreciated, as the material removal element 122 is rotated, the maximum amplitude A of the debriding member 124 defines the maximum opening created in the occlusion O.

Figure 5D:
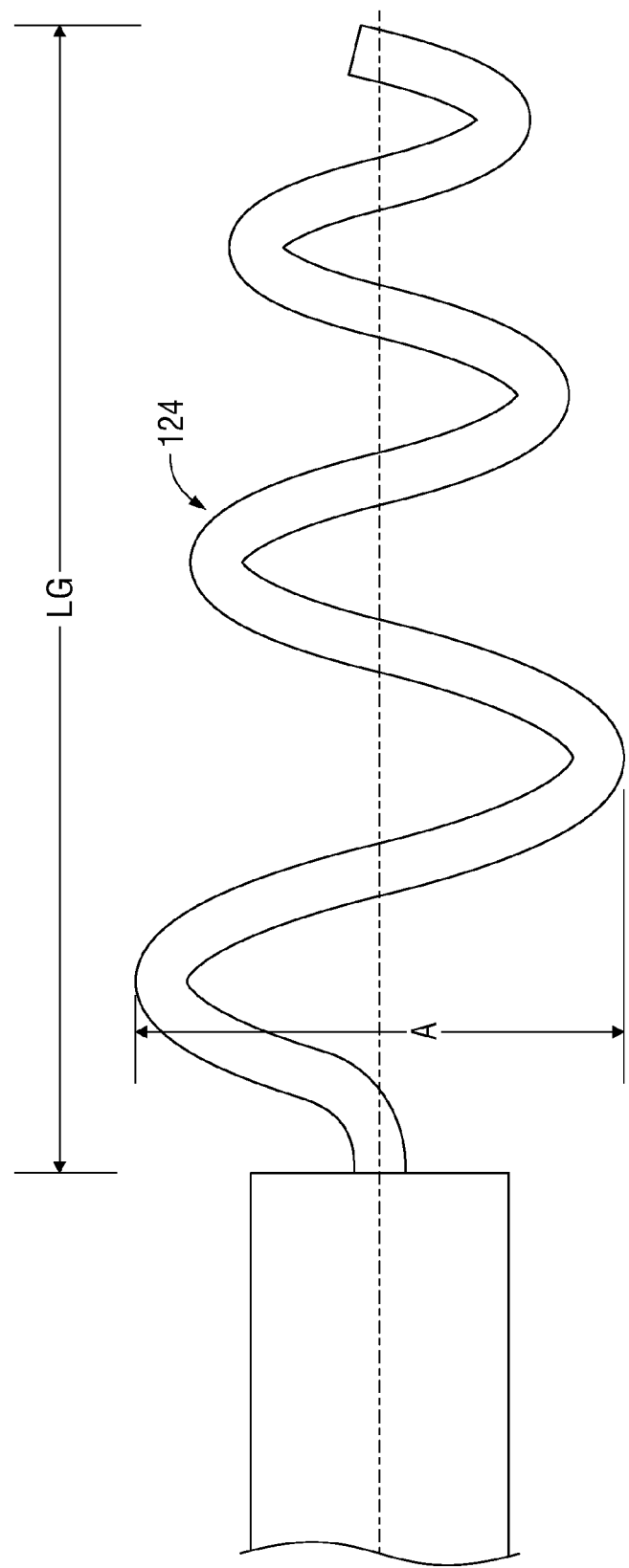
FIG. 5D is a partial, side view illustrating a material removal element of the occlusion treatment device according to another embodiment of the disclosure.

With reference to FIG. 5D, in one embodiment of the disclosure, it is envisioned that the amplitude A of the debriding member 124 may be varied along the length LG of the debriding member 124, in contrast to the embodiments illustrated in FIGS. 5A and 5B, for example, wherein the amplitude A of the debriding member 124 remains constant over the length LG of the debriding member 124. In the specific embodiment illustrated in FIG. 5D, the amplitude A of the debriding member 124 is illustrated as decreasing in a distal direction, whereby the likelihood that the debriding member 124 will interface with the lumen L (see FIG. 5C) is decreased. It should be appreciated, however, that in an alternative embodiment of the disclosure, the amplitude A of the debriding member 124 may increase in a distal direction without departing from the scope of the present disclosure.

With reference now to FIG. 1 in particular, the control unit 109 will be described. The control unit 109 regulates operation of the occlusion treatment device 100, as well as the other components of the occlusion treatment system 1000, and thus, may include various microprocessor, electronic components, software, and/or firmware components. Software may be provided in a machine-readable medium storing executable code and/or other data in order to facilitate processing of user-specific data.

One specific function of the control unit 109 is to provide the user with feedback from the occlusion treatment device 100, and/or information pertaining to environmental conditions, operating parameters, etc. The control unit 109 may be configured to output operational information concerning such feedback and information to the user. For example, the control unit may be configured to monitor the position and/or movement of the material removal element 122, as well as the temperature at the target site, aspiration rate and/or volume, infusion rate and/or volume, elapsed time, or any other physical parameter desired.

It is further envisioned that the control unit 109 may implement certain automated, and/or selectable, control features. For example, various routines or programs including operating parameters may be preselected, stored and selectable by the user, thereby permitting the user to input specified parameters and data. Thus, according to one embodiment of the disclosure, the control unit 109 may control features, and/or operation, of the occlusion treatment device 100 based on the data or information input by the user. For example, the user may input data concerning the occlusion O, such as the dimension of the occlusion O, the type of tissue comprising the occlusion O, rate of blood flow, volume of blood flow, percentage of restriction, the type of lumen L that is occluded, for example, a blood vessel, the location of the lumen L, particular dimensions of the lumen L, desired advance rate, desired aspiration and/or infusion rates, or any other data useful to the specific procedure. Based on the data input by the user, the control unit 109 may calculate and implement automated operating conditions in order to automatically regulate, for example, the temperature of the material removal element 122. Various operating parameters, operating conditions, patient conditions, and the like may also be recorded and stored within the control unit 109 so as to preserve a record of the patient, and the details of the procedure.

A method of treating the occlusion O with the occlusion treatment system 1000 will now be discussed with reference to FIGS. 1-3B and 6-8. Initially, the occlusion treatment device 100 is inserted into the lumen L, and advanced until the material removal element 122, and the electrode(s) 126, are positioned adjacent the occlusion O, as seen in FIG. 6. In certain embodiments, positioning of the occlusion treatment device 100 may be aided through the use of a guidewire 134 coaxially positionable within the catheter 110, as illustrated in FIG. 1. If utilized, the guidewire 134 is initially positioned within the lumen L, for example, through the use of a needle cannula (not shown), as is known in the art. Thereafter, the guidewire 134 is advanced to a desired location adjacent the occlusion O, and a proximal end of the guidewire 134 is inserted into a distal end of the catheter 110, for example through passageway 118, such that the catheter 110 can be advanced distally over the guidewire 134. A dilator/sheath assembly (not shown) may also be used to further facilitate insertion of the occlusion treatment device 100 into the lumen L.

Following positioning of the occlusion treatment device 100 in the desired manner, the expandable elements 120$_A$, 120$_B$ are expanded, as seen in FIG. 7, in order to properly orient, and maintain, the position of the occlusion treatment device 100 within the lumen L. It is envisioned that the expandable elements 120$_A$, 120$_B$ may be expanded to the same extent, or alternatively, that the expandable elements 120$_A$, 120$_B$ may be expanded to differing extents for reasons that will be detailed below.

After expansion of the expandable elements 120$_A$, 120$_B$, the energy source 102 (FIG. 1) is activated to supply energy to the electrode(s) 126 which are positioned on the outer surface 128 of the body 125 of the debriding member 124. In order to facilitate debriding of the occlusion O, and thus, the creation of an opening 136 in the occlusion O, the material removal element 122 is manipulated to move the debriding member 124 in relation to the occlusion O to enable the electrodes 126 to act upon the occlusion O. The energy supplied to the electrodes 126 may soften or break the occlusion O. During debridement of the occlusion O, debris can be aspirated via the passageway 118 extending through the catheter 110 using the fluid suction/supply device 108 (FIG. 1). Specifically, debris from the occlusion O can be drawn into and through the passageway 118, via a vacuum force created by the fluid suction/supply device 108 in order to remove the debris from the lumen L. In this regard, the expandable elements 120$_A$, 120$_B$ may have the secondary benefit of preventing debris from migrating along the lumen away from the occlusion, as well as preventing the passageway 118 from suctioning other fluid, such as blood, out of the lumen. In alternative embodiments with multiple passageways, one passageway may continually supply fluid while the other passageway continually suctions the fluid and debris away from the occlusion O.

Treatment of the occlusion O can be further facilitated through the application of mechanical force to the occlusion O via reciprocal axial movement, and/or rotation, of the material removal element 122. For the embodiment in which the material removal element 122 is secured to the distal end 116 of the catheter 110, the catheter 110 may be either manipulated manually by the user, or alternatively, that manipulation of the catheter 110 may be effected by a drive mechanism (not shown) operatively connected to the control unit 109 so as to automate movement of the catheter 110. In the embodiment in which the material removal element 122 is a separate component inserted through the passageway 118, the material removal element 122 may be manipulated manually by the user or, alternatively, by a drive mechanism. In either case, the material removal element 122 may be rotated and/or pushed into the occlusion to burrow the device through the occlusion O (FIGS. 8-9). This burrowing may occur due to mechanical and/or electrical action.

Debriding of the occlusion O continues until the material removal element 122 penetrates into the occlusion O. Thereafter, the catheter 110 can be advanced through the occlusion O in order to facilitate further treatment, for example, through the placement of a stent, or the delivery of a therapeutic agent. In order to facilitate advancement of the catheter 110 through the lumen L, and the opening 136 (FIG. 8) in the occlusion O while the expandable elements 120$_A$, 120$_B$ are expanded, it is envisioned that the expandable elements 120$_A$, 120$_B$, and/or the remaining portions of the catheter 110, may include a lubricous coating. Alternatively, the expandable elements 120$_A$, 120$_B$ may be slightly deflated, the catheter 110 advanced, and the expandable elements 120$_A$, 120$_B$ re-inflated.

In one embodiment of the disclosure, the source of pressurized fluid 106 facilitating expansion of the expandable elements 120$_A$, 120$_B$ may be common to each of the expandable elements 120$_A$, 120$_B$, whereby the expandable elements 120$_A$, 120$_B$ are uniformly expanded, as seen in FIGS. 7 and 8, for example. Alternatively, it is envisioned that the expandable elements 120$_A$, 120$_B$ may be connected to separate sources of pressurized fluid 106, whereby the expandable elements $120_A$, $120_B$ may be expanded independently of each other such that the expandable elements $120_A$, $120_B$ may be expanded to varying extents, if desired. For example, as seen in FIG. 9, it may be desirable to expand the proximal expandable element $120_A$ completely while only partially expanding the distal expandable element $120_B$ in order to allow the distal expandable element $120_B$ to maintain a greater measure of pliability and deformability, and thereby permit the distal expandable element $120_B$ to enter, and pass through, the opening 136 (FIGS. 8, 9) created in the occlusion O by the material removal element 122.

In such embodiments, the expandable element $120_B$ may be configured, dimensioned, and adapted to contribute to debridement of the occlusion O, and thus, expansion of the opening 136. For example, the distal expandable element $120_B$ may be formed from a material more rigid than that comprising the proximal expandable element $120_A$, thereby increasing the ability of the distal expandable element $120_B$ to engage, and debride, the occlusion O (FIG. 8). Additionally, or alternatively, the distal expandable element $120_B$ may include one or more cutting elements 138 positioned on an outer surface thereof, as seen in FIG. 9. The cutting elements 138 may be formed from any material suitable for the intended purpose of facilitating debriding of the occlusion O, such as, for example tungsten, carbide, nitinol or stainless steel. The cutting elements 138 may be directionally faced so that one face or portion of the cutting elements 138 actually cuts the occlusion. Such a configuration may add safety to the device by not enabling all portions of the cutting elements 138 to cut, particularly those portions that could potentially contact the lumen L.

Through reference to the foregoing description, it should be understood that each embodiment of the occlusion treatment device is capable of both mechanical and non-mechanical treatment of an occlusion. As indicated above, certain types of occlusive tissue are more amenable to certain methods of removal. For example, chronic clots, as compared to acute clots, cannot be effectively removed using solely chemical agents such as tPA. Accordingly, the treatment capabilities of the occlusion treatment device disclosed herein can be used alone or in combination with other capabilities to effectively remove occlusive tissue within a body vessel. For example, where the occlusive tissue is a chronic clot, the clot can be effectively removed using the electrical and mechanical capabilities of the occlusion treatment device. As an additional example, it is not beyond the scope of the present disclosure to treat an occlusion mechanically, electrically, and chemically via manipulation of the occlusion treatment device in the manner described above, and the delivery of a therapeutic agent through passageway 118, or another passageway in the catheter 110.

Persons skilled in the art will understand that the devices and methods specifically described herein and illustrated in the accompanying drawings are non-limiting, exemplary embodiments. It is envisioned that the elements and features illustrated or described in connection with one exemplary embodiment may be combined with those of another embodiment without departing from the scope of the present disclosure. As well, one skilled in the art will appreciate further features and advantages of the presently disclosed occlusion treatment system based on the above-described embodiments. Accordingly, the present disclosure is not to be limited by what has been particularly shown and described, except as indicated by the appended claims.

The invention claimed is:

1. An occlusion treatment device configured and dimensioned for treatment of a lumen at least partially blocked by an occlusion, the occlusion treatment device comprising:
   a catheter including a body portion having proximal and distal ends;
   at least one expandable element secured to the body portion of the catheter, the at least one expandable element being expandable within the lumen to define a radial dimension; and
   a material removal element configured to extend distally from the distal end of the body portion and including a flexible debriding member having a free distal end configured and dimensioned to contact the occlusion, wherein a maximum exposed distal portion of the material removal element defines a length less than the radial dimension in order to restrict contact between the flexible debriding member and an inner wall of the lumen, and being in communication with an energy source to facilitate selective energizing of the flexible debriding member, the catheter being dimensioned to be axially movable through the lumen, and rotatable within the lumen, such that the material removal element selectively imparts at least one of a non-mechanical energy and a mechanical energy to the occlusion to effect debriding of the occlusion.

2. The occlusion treatment device of claim 1, wherein the body portion of the catheter and the material removal element are formed from different materials.

3. The occlusion treatment device of claim 1, wherein the material comprising the material removal element is more rigid than the material comprising the body portion of the catheter.

4. The occlusion treatment device of claim 1, wherein the debriding member includes at least one electrode in communication with the energy source.

5. The occlusion treatment device of claim 1, wherein the material removal element is movable through the body portion of the catheter.

6. The occlusion treatment device of claim 1, further including a ground element in communication with the energy source, the ground element being configured and dimensioned for contact with a patient's tissue.

7. The occlusion treatment device of claim 1, wherein the flexible debriding member includes a plurality of electrodes, at least two electrodes of the plurality of electrodes being at different axial positions along the length of the flexible debriding member.

8. A method of treating a lumen at least partially blocked by an occlusion comprising: positioning an occlusion treatment device within the lumen;
   advancing the occlusion treatment device through the lumen until a free distal end of a flexible material removal element of the device is positioned adjacent the occlusion;
   expanding an expandable element of the occlusion treatment device to define a radial dimension;
   penetrating the occlusion with the free distal end of the material removal element to create an opening;
   delivering non-mechanical energy to the material removal element;
   advancing the material removal element distally through the opening; and
   manipulating the material removal element to impart at least one of a non-mechanical energy and a mechanical energy to the occlusion to effect debriding of the occlusion and enlargement of the opening;

wherein the material removal element has a maximum exposed distal portion defining a length less than the radial dimension in order to restrict contact between the material removal element and an inner wall of the lumen.

9. The method of claim 8, wherein manipulating the material removal element includes rotating the material removal element.

10. The method of claim 8, wherein manipulating the material removal element includes effecting axial movement of the material removal element.

11. The method of claim 8, wherein expanding the expandable element includes expanding a proximal expandable element to center the occlusion treatment device within the lumen, and expanding a distal expandable element.

12. The method of claim 11, wherein expanding the expandable element includes expanding the proximal expandable element to a first extent, and expanding the distal expandable element to a second, lesser extent.

13. The method of claim 12, further including advancing the occlusion treatment device through the lumen such that the expandable element is at least partially positioned within an opening in the occlusion created during debriding of the occlusion.

14. The method of claim 13, further including mechanically debriding the occlusion using the expandable element.

15. An occlusion treatment device configured and dimensioned for treatment of a lumen at least partially blocked by an occlusion, the occlusion treatment device comprising:
 a catheter including a body portion having proximal and distal ends;
 at least one expandable element secured to the body portion of the catheter, the at least one expandable element being within the lumen to define a radial dimension; and
 a material removal element configured to extend distally from the distal end of the body portion and including a flexible debriding member, wherein a maximum exposed distal portion of the material removal element defines a length less than the radial dimension in order to restrict contact between the flexible debriding member and an inner wall of the lumen.

16. The occlusion treatment device of claim 15, wherein the debriding member includes a free distal end configured and dimensioned to contact the occlusion.

17. The occlusion treatment device of claim 15, wherein the material removal element is in communication with an energy source to facilitate selective energizing of the debriding member.

18. The occlusion treatment device of claim 17, wherein the catheter is dimensioned to be axially movable through the lumen and rotatable within the lumen such that the material removal element selectively imparts at least one of a non-mechanical energy and mechanical energy to the occlusion to effect debriding of the occlusion.

19. The occlusion treatment device of claim 1 wherein the flexible debriding member has a non-linear configuration defining an amplitude that varies along a length of the debriding member.

20. The occlusion treatment device of claim 19, wherein the amplitude defined by the debriding member decreases in a distal direction.

* * * * *